United States Patent
Tralshawala et al.

(10) Patent No.: US 7,911,205 B2
(45) Date of Patent: Mar. 22, 2011

(54) ELECTROMAGNETIC RESONANCE FREQUENCY INSPECTION SYSTEMS AND METHODS

(75) Inventors: Nilesh Tralshawala, Rexford, NY (US); Yuri Alexeyevich Plotnikov, Niskayuna, NY (US)

(73) Assignee: General Electric Company, Niskayuna, NY (US)

(*) Notice: Subject to any disclaimer, the term of this patent is extended or adjusted under 35 U.S.C. 154(b) by 797 days.

(21) Appl. No.: 11/860,629

(22) Filed: Sep. 25, 2007

(65) Prior Publication Data

US 2009/0079424 A1  Mar. 26, 2009

(51) Int. Cl.
- *G01R 33/14* (2006.01)
- *G01R 35/00* (2006.01)
- *G01N 27/72* (2006.01)

(52) U.S. Cl. .................. 324/222; 324/202; 324/228
(58) Field of Classification Search ............ 324/222, 324/202, 228
See application file for complete search history.

(56) References Cited

U.S. PATENT DOCUMENTS

| | | | |
|---|---|---|---|
| 4,303,885 A * | 12/1981 | Davis et al. | ........ 324/237 |
| 5,659,248 A | 8/1997 | Hedengren et al. | |
| 6,657,429 B1 | 12/2003 | Goldfine et al. | |
| 6,670,808 B2 | 12/2003 | Nath et al. | |
| 2004/0066188 A1 | 4/2004 | Goldfine et al. | |
| 2006/0009865 A1 | 1/2006 | Goldfine et al. | |
| 2006/0244443 A1 | 11/2006 | Goldfine et al. | |

OTHER PUBLICATIONS

C. V. Dodd & W. E. Deeds; "Analytical Solutions to Eddy-Current Probe-Coil Problems"; Journal of Applied Physics, vol. 39, No. 6; May 1968; pp. 2829-2838.

* cited by examiner

*Primary Examiner* — Reena Aurora
(74) *Attorney, Agent, or Firm* — Penny A. Clarke

(57) ABSTRACT

A method of inspecting a test part is provided. The method includes positioning a coil on a surface of the test part and exciting the coil at a resonance frequency. The method also includes determining at least one of a resonance frequency shift and a quality factor of the coil and estimating an electrical conductivity of the test part based on at least one of the resonance frequency shift and the quality factor of the coil. The method further includes obtaining depth profile of residual stress using conductivity measurements at various resonance frequencies.

21 Claims, 7 Drawing Sheets

ELECTROMAGNETIC RESONANCE FREQUENCY INSPECTION SYSTEMS AND METHODS

BACKGROUND

The invention relates generally to inspection systems and methods, and, more particularly to, electromagnetic resonance frequency inspection systems and methods for estimating material properties of a part.

Components such as aircraft engine parts can be protected from developing microcracks by stressing the surface layer of the part using shotpeening. Very briefly, shotpeening involves bombarding the surface of the part with small spherical media called shot. Each piece of shot striking the surface imparts a small indentation to the part. In order for the indentation to be created, the surface of the part must be yielded in tension. Further, below the surface, the material tries to restore its original shape, thereby producing a hemisphere of material that is highly stressed in compression. Monitoring of material properties of shotpeened parts is desirable to determine how long the part can be used before it needs to be re-shotpeened. For example, it is desirable to monitor the shotpeen residual stress depth profile of the part to assess the need for re-shotpeening of the part.

Typically, a destructive evaluation of the shotpeened part is performed to estimate the material properties of the part. However, this technique makes the part unusable and therefore requires replacement of the part. In other applications, certain shotpeened parts may be re-shotpeened at select time intervals without assessing the need for re-shotpeening the part.

Accordingly, it would be desirable to develop estimation techniques that provide accurate estimation of material properties of a part. Particularly, it will be advantageous to develop a technique for accurate estimation of the material properties of a shotpeened part without damaging the part.

BRIEF DESCRIPTION

Briefly, according to one embodiment of the invention, a method of inspecting a test part is provided. The method includes positioning a coil on a surface of the test part and exciting the coil at a resonance frequency. The method also includes determining at least one of a resonance frequency shift and a quality factor of the eddy current coil and estimating an electrical conductivity of the test part based on at least one of the resonance frequency shift and the quality factor of the coil.

In another embodiment, an electromagnetic resonance frequency system for inspecting a test part is provided. The system includes a coil configured to scan the test part at a resonance frequency and a processor configured to estimate an electrical conductivity based upon at least one of a measured resonance frequency shift and a quality factor of the coil.

In another embodiment, a method of inspecting a test part is provided. The method includes selecting at least one coil having a size within a pre-determined operating range and positioning the at least one coil on a surface of the test part. The method also includes exciting the at least one coil at a plurality of resonance frequencies and determining a quality factor of the at least one coil based upon a measured impedance of the coil to estimate an electrical conductivity of the test part. The size of the at least one coil is selected such that a resistive component of the impedance of the coil increases with the electrical conductivity of the test part.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
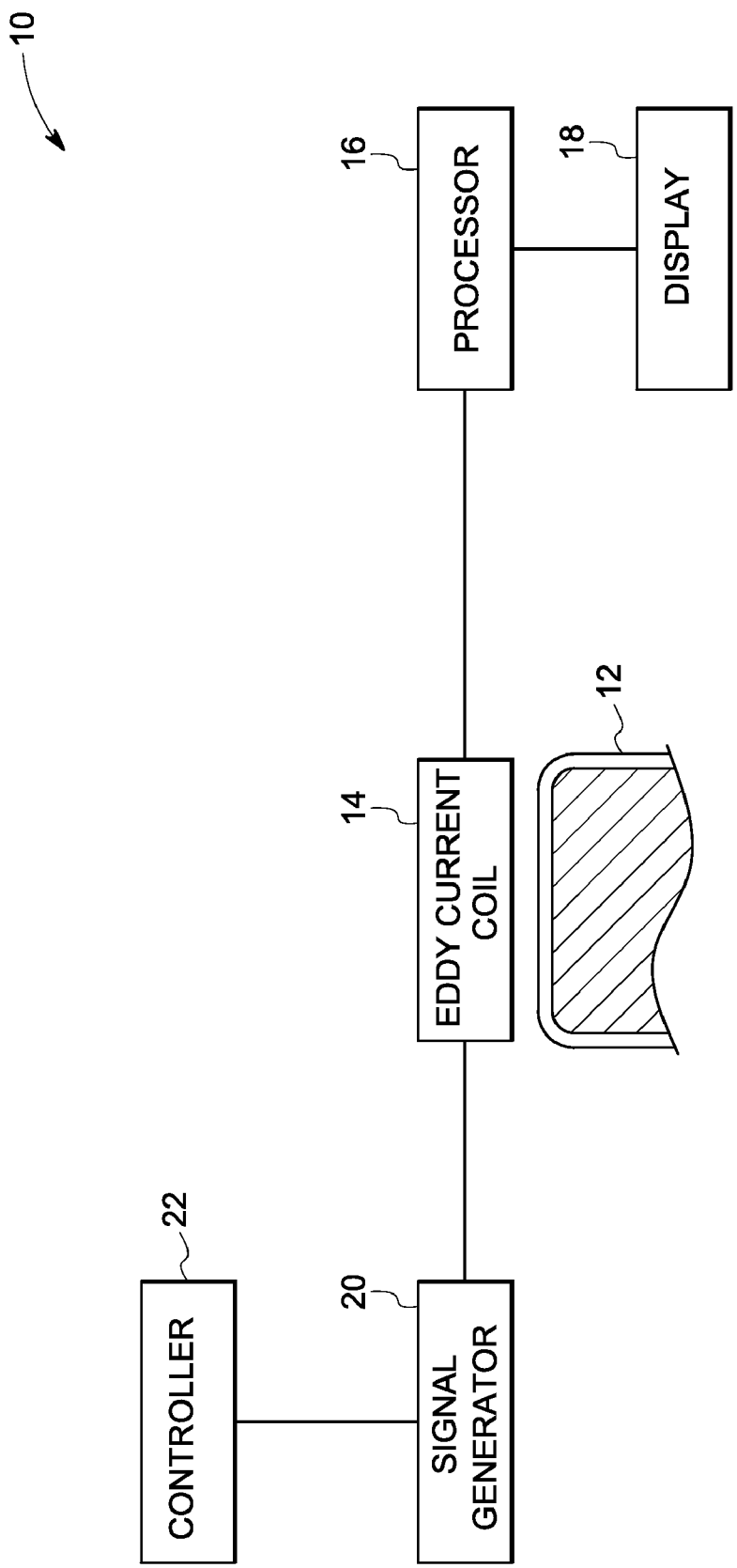
FIG. 1 is a diagrammatical representation of an electromagnetic resonance frequency inspection system for estimating material properties of a test part.
Figure 2:
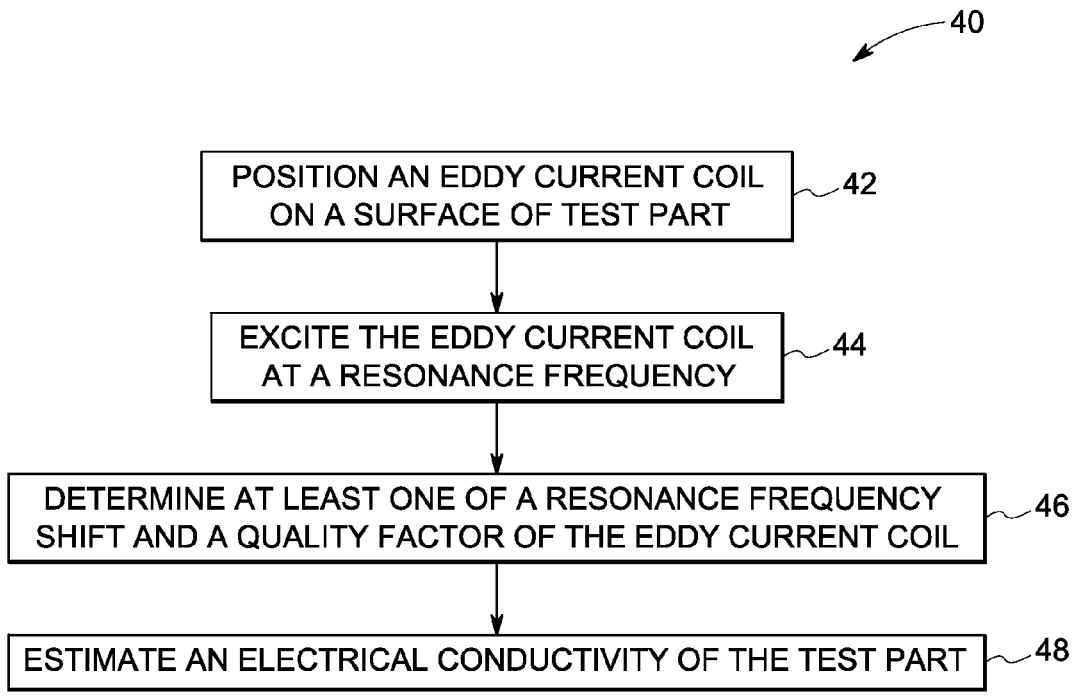
FIG. 2 is a flow chart illustrating an exemplary electromagnetic resonance frequency inspection method.

As discussed in detail below, embodiments of the present invention function to provide an inspection technique that provides an estimation of material properties of a part. In particular, the present invention facilitates accurate estimation of material properties of a shotpeened part using an electromagnetic resonance frequency inspection system. FIG. 1 is a diagrammatical representation of an electromagnetic resonance frequency inspection system 10 for estimating material properties of a test part 12. The electromagnetic resonance frequency inspection system 10 includes a coil 14 configured to scan the test part 12. In this exemplary embodiment, the coil 14 comprises an eddy current coil 14 that is excited at a resonance frequency to scan the test part 12. In certain embodiments, the test part 12 comprises a shotpeened part.

Further, the electromagnetic resonance frequency inspection system 10 includes a processor 16 configured to estimate an electrical conductivity of the test part 12 based upon at least one of a measured resonance frequency shift and a quality factor of the eddy current coil 14. As used herein, the term "quality factor" refers to a ratio of energy stored per cycle to energy dissipated per cycle of the eddy current coil. Further, the term "resonance frequency shift" refers to a change in resonance frequency of the eddy current coil 14. It should be noted that the present invention is not limited to any particular processor for performing the processing tasks of the invention. The term "processor," as that term is used herein, is intended to denote any machine capable of performing the calculations, or computations, necessary to perform the tasks of the invention. The term "processor" is intended to denote any machine that is capable of accepting a structured input and of processing the input in accordance with prescribed rules to produce an output. It should also be noted that the phrase "configured to" as used herein means that the processor is equipped with a combination of hardware and software for performing the tasks of the invention, as will be understood by those skilled in the art.

The electromagnetic resonance frequency inspection system 10 may include a display 18 for displaying material properties such as the estimated electrical conductivity of the test part 12 to a user of the system 10. The electromagnetic resonance frequency inspection system 10 also includes a signal generator 20 configured to energize the eddy current coil 14 at a plurality of frequencies. In certain embodiments, a controller 22 may be employed to control the signal generator 20.

Figure 4:
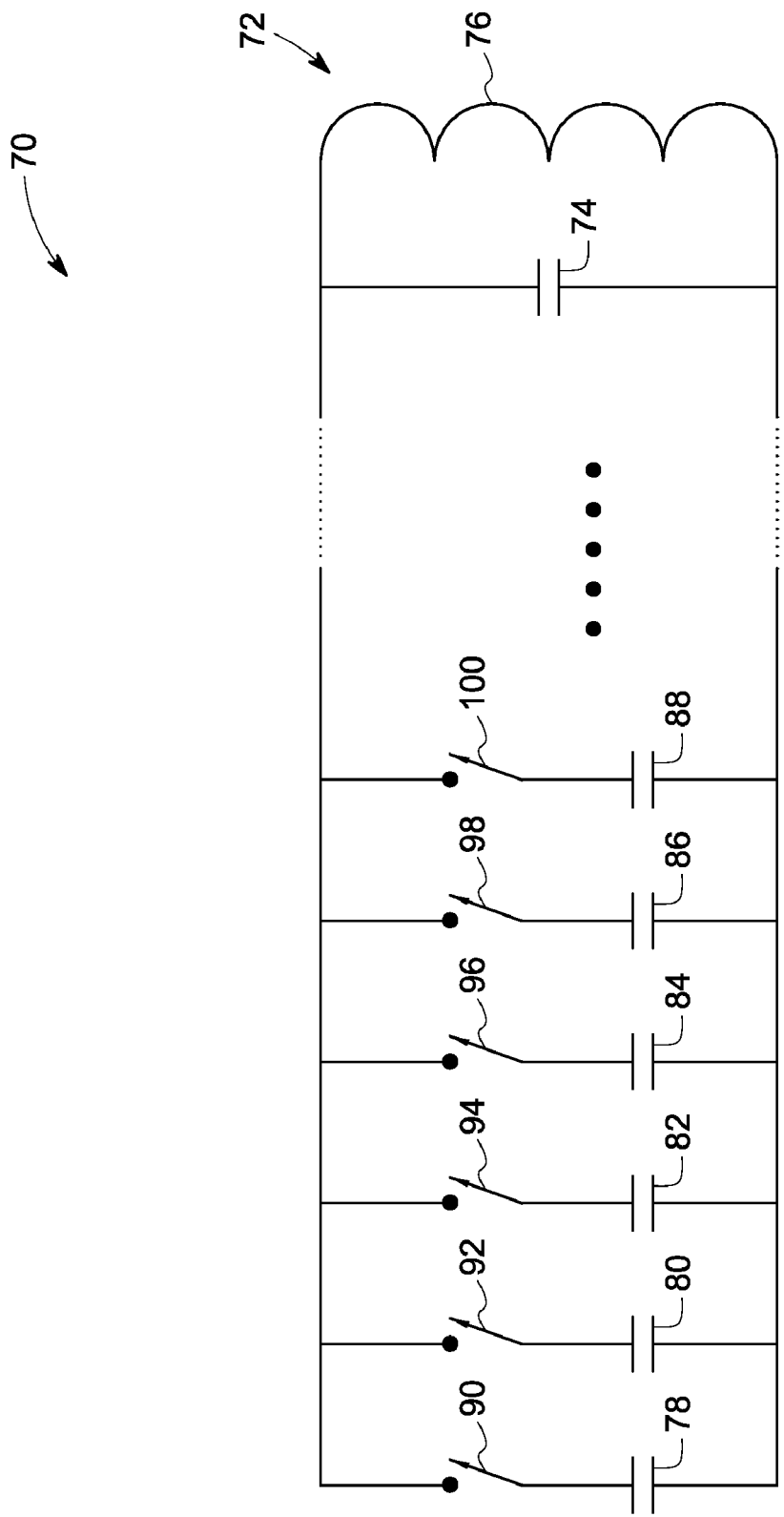
FIG. 4 is a diagrammatical representation of an exemplary equivalent electrical circuit of a coil employed in the electromagnetic resonance frequency inspection system of FIG. 1.

As described above, the signal generator 20 is configured to energize the eddy current coil 14 at a plurality of frequencies. In one exemplary embodiment, the electromagnetic resonance frequency inspection system 10 includes a plurality of eddy current coils (not shown) and the signal generator 20 is configured to energize each of the eddy current coils at respective ones of the frequencies. An exemplary equivalent electrical circuit of the eddy current coil 14 employed in the electromagnetic resonance frequency inspection system 10 is shown in FIG. 4. As shown for example in FIG. 4, the resonance probe (indicated by reference number 70 in FIG. 5) includes an eddy current coil 72 and a plurality of capacitors 78, 80, 82, 84, 86 and 88 coupled to the eddy current coil 72. Further, a plurality of switches 90, 92, 94, 96, 98 and 100 may be employed to selectively couple respective ones of the capacitors 78, 80, 82, 84, 86 and 88 to the eddy current coil 72 to adjust a resonance frequency of the eddy current probe 70. Further, in certain embodiments, the resonance probe 14 may include a variable capacitor (not shown) coupled to the eddy current coil for adjusting the resonance frequency of the eddy current coil 14.

Figure 3:
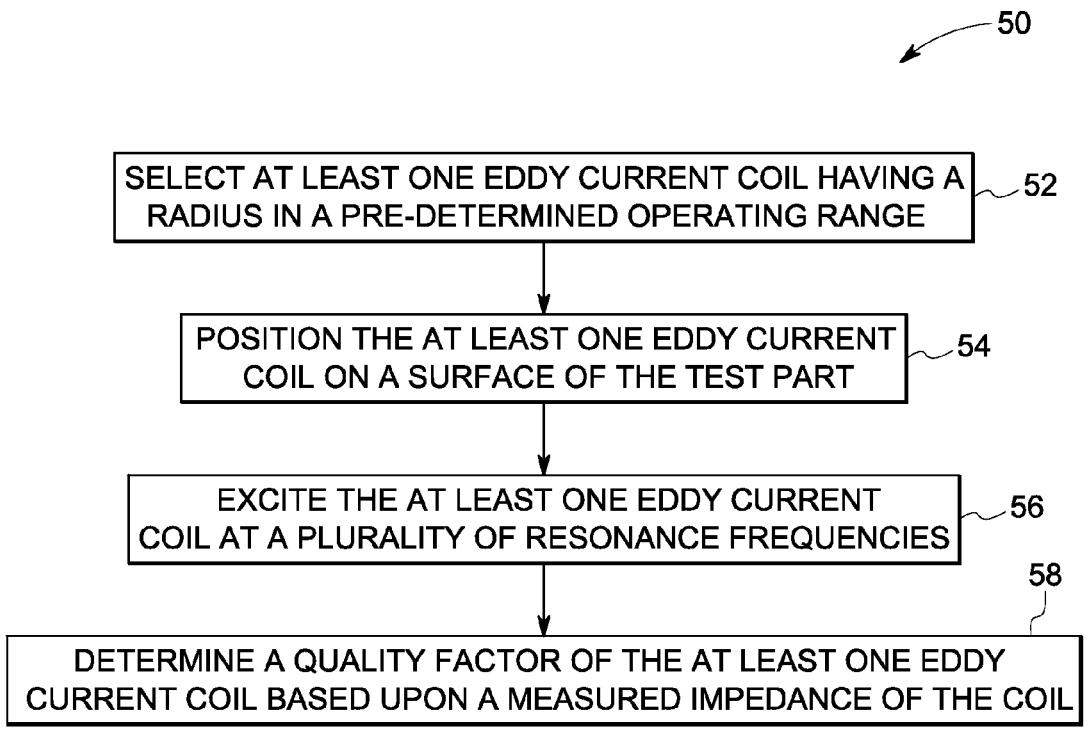
FIG. 3 is a flow chart illustrating another exemplary electromagnetic resonance frequency inspection method.

FIG. 3 is a flow chart illustrating an exemplary electromagnetic resonance frequency inspection method 40. At step 42, an eddy current coil is positioned on a surface of a test part. Examples of the eddy current coil include single eddy current array probes (SECAPs), or eddy current array probes (ECAPs). Further, the eddy current coil is excited at a resonance frequency (step 44). At step 46, at least one of a resonance frequency shift and a quality factor of eddy current coil is determined. Moreover, an electrical conductivity of the test part is estimated based upon at least one of the resonance frequency shift and the quality factor of the eddy current coil.

In certain embodiments, the resonance frequency of the eddy current coil is adjusted multiple times. In one embodiment, the eddy current coil is excited at a plurality of respective resonance frequencies. In this exemplary embodiment, the frequency of the eddy current coil is tuned using switched capacitive banks (see FIG. 4) or by using variable capacitors. Further, at least one of the resonance frequency shift and the quality factor of the eddy current coil is determined. In certain embodiments, a plurality of eddy current coils operating at different frequencies are employed, and the resonance frequency versus the quality factor relationship may be determined.

The quality factor for the eddy current coil as described above is related to the conductivity of the part under test. Therefore, using the quality factor a frequency versus conductivity profile may be generated. It should be noted that at lower frequencies the eddy current coil senses deeper into the material under test and as the resonance frequency is progressively increased, the shallower material region is being sensed using the eddy current coil. Thus, by carrying out measurements at multiple frequencies, a depth profile of conductivity is obtained. In this exemplary embodiment, a conductivity depth profile is obtained for the test part based upon measurements carried out by varying the resonance frequency of the coil. As used herein, the term "conductivity depth profile" refers to profile of electrical conductivity of the test part at different depths of the test part.

Moreover, a residual stress profile for the test part may be generated from the conductivity depth profile. In certain embodiments, the residual stress profile is generated by relating the conductivity depth profile for the test part to residual stress profile data. In one example, the residual stress profile data is obtained by x-ray diffraction (XRD) testing. Advantageously, the conductivity depth profile and the residual stress profile may be utilized to assess the need for replacing or re-shotpeening the test part.

FIG. 3 is a flow chart illustrating another exemplary electromagnetic resonance frequency inspection method 50. At step 52, at least one eddy current coil having a size in a pre-determined operating range is selected. In certain embodiments, a radius of a circular coil is selected in a pre-determined operating range. In this exemplary embodiment, the radius of the at least one eddy current coil is selected such that a resistive component (R) of an impedance (Z) of the coil increases with the electrical conductivity of the test part. The selection of the radius of the eddy current coil will be described below with reference to FIG. 6. It should be noted that the coils may have different shapes such as rectangular, square and so forth and an effective size of such coils is selected in this embodiment. Further, the at least one eddy current coil is positioned on a surface of the test part (step 54). At step 56, the at least one eddy current coil is excited at a plurality of resonance frequencies. Further, the quality factor of the at least one eddy current coil is determined based upon a measured impedance of the eddy current coil (step 58). In certain embodiments, a resonance frequency shift of the eddy current coil is measured to estimate the electrical conductivity of the test part. Moreover, a conductivity depth profile may be obtained based upon the quality factor or the resonance frequency shift of the eddy current coil at the respective resonance frequencies.

As described above, the eddy current coil 14 (see FIG. 1) is energized at a plurality of resonance frequencies to obtain a conductivity depth profile of the test part 12. FIG. 4 is a diagrammatical representation of an exemplary equivalent electrical circuit 70 of an eddy current coil 14 employed in the electromagnetic resonance frequency inspection system 10 of FIG. 1. As shown, the circuit 70 includes an eddy current coil 72 having a capacitance 74 (C') and an inductance 76 (L). Further, a plurality of capacitors such as represented by reference numerals 78, 80, 82, 84, 86 and 88 may be coupled to the eddy current coil 72 for energizing the eddy current coil 72 at a plurality of resonance frequencies. In this example, six capacitors are coupled to the eddy current coil 72. However, a greater or a lesser number of capacitors may be employed to change the resonance frequency of the eddy current coil 72. In certain embodiments, one or more of these capacitors include variable capacitors for continuously changing the resonance frequency of the coil 72.

Further, a plurality of switches such as represented by reference numerals 90, 92, 94, 96, 98 and 100 may be employed to selectively couple or decouple the capacitors 78, 80, 82, 84, 86 and 88 to the eddy current coil 72 for operating the eddy current coil at a particular resonance frequency. In this embodiment, the resonance frequency of the coil 72 is represented by the following equation:

$$\omega_n = \frac{1}{\sqrt{(C' + C_n)L}} \qquad (1)$$

where
- $\omega_n$ is the resonance frequency of the eddy current coil 72;
- C is the self capacitance of the eddy current coil 72;
- $C_n$ is the capacitance of the $n^{th}$ capacitor coupled to the eddy current coil 72; and
- L is the inductance of the eddy current coil 72.

Figure 5:
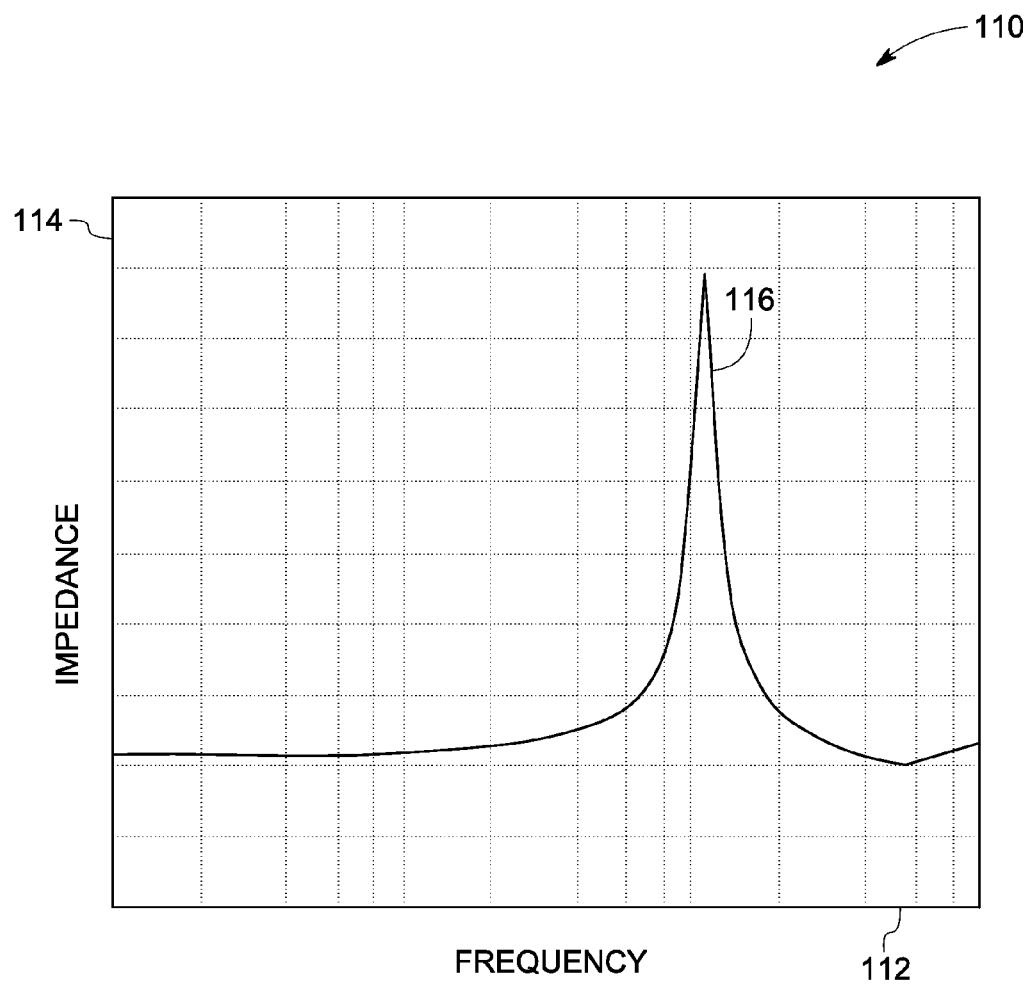
FIG. 5 is a graphical representation of exemplary results for resonance frequencies and quality factor for the eddy current coil employed in the electromagnetic resonance frequency inspection system of FIG. 1.

In this exemplary embodiment, a conductivity depth profile is obtained for the test part 12 based upon the resonance frequency shifts and/or the quality factors of the coil 72 at the respective resonance frequencies. FIG. 5 is a graphical representation of exemplary results 110 for resonance frequencies and quality factor for the eddy current coil 14 employed in the electromagnetic resonance frequency inspection system 10 of FIG. 1. In certain embodiments, signals from the eddy current coil 14 are directed to an impedance analyzer for determining the resonance frequency shifts and the quality factors of the coil 14. The abscissa axis represents a frequency 112 and the ordinate axis represents an impedance 114 of the coil 14. In this exemplary embodiment, the signal from the coil 14 is represented by reference numeral 116. In this exemplary embodiment, the resonance frequency shift and the quality factor of the signal 112 are determined by the impedance analyzer. These factors are further utilized to estimate the conductivity of the test part 12. In this exemplary embodiment, the peak of the signal 112 is indicative of the resonance frequency and a width of the peak of the signal 112 is indicative of the quality factor of the eddy current coil 14.

In certain embodiments, at least one eddy current coil 14 is selected to have a size in a pre-determined operating range. In particular, the size of the at least one eddy current coil is selected such that a resistive component R of an impedance (Z=R+iX, where X is the reactive component) of the coil increases with the electrical conductivity of the test part 12.

Figure 6:
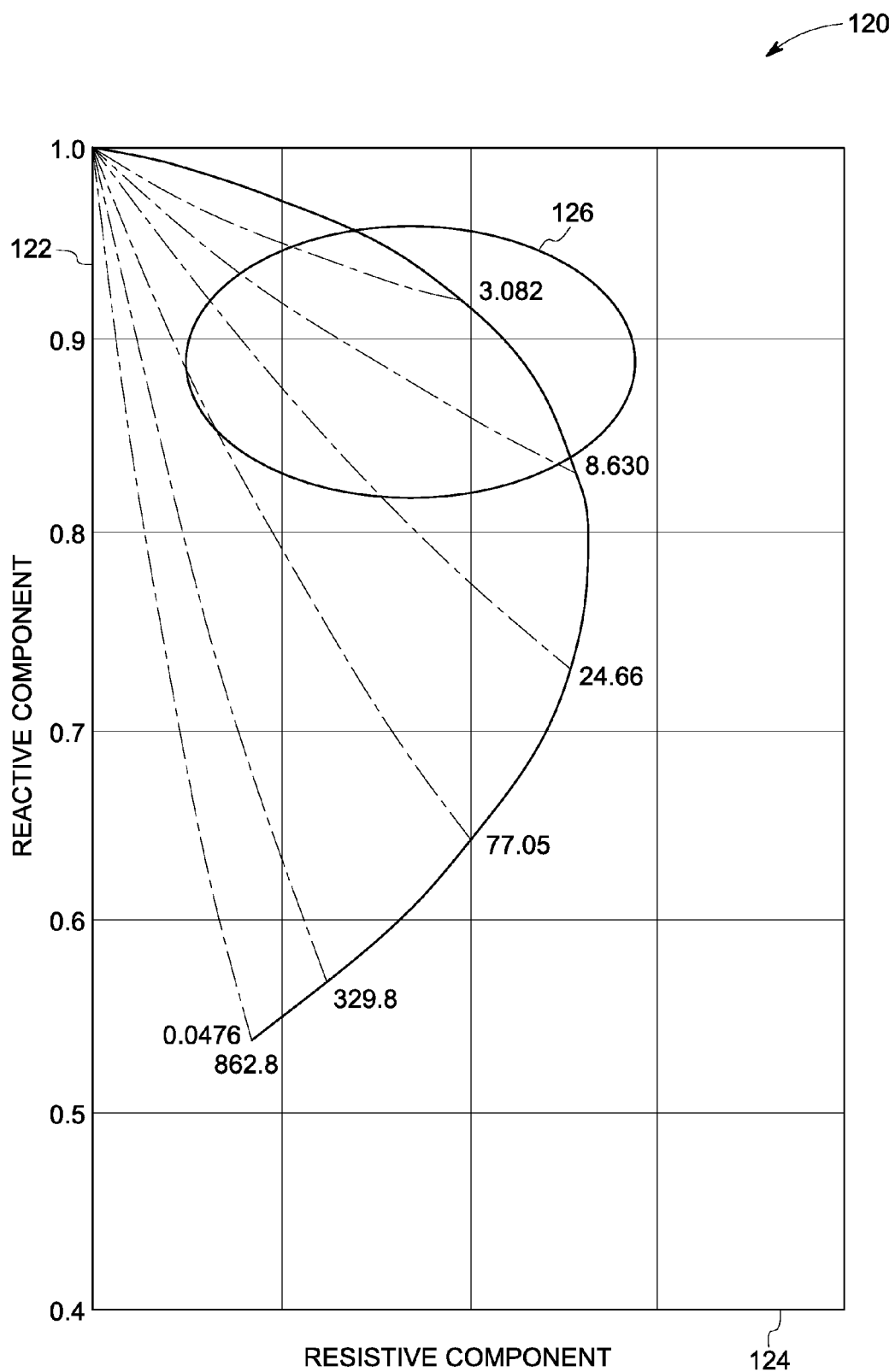
FIG. 6 is a graphical representation of an impedance profile for the eddy current coil employed in the electromagnetic resonance frequency inspection system of FIG. 1.

FIG. 6 is a graphical representation of an impedance profile 120 for the eddy current coil 14 employed in the electromagnetic resonance frequency inspection system 10 of FIG. 1. The ordinate axis represents a reactive component X=ωL and the abscissa axis represents a resistive component R of the eddy current coil 14. In this exemplary embodiment, a Dodd-Deeds model is employed to estimate the conductivity of the test part 12 (see FIG. 1). In particular, the quality factor and the resonance shifts are related to the conductivity of the test part 12. In this exemplary embodiment, the resonance frequency of the eddy current coil 14 is represented by the following equation:

$$\omega_0 = \frac{1}{\sqrt{LC}} \qquad (2)$$

where:
- $\omega_0$ is the resonance frequency of the eddy current coil 14;
- L is the inductance of the eddy current coil 14; and
- C=C'+$C_n$ is the total capacitance of the eddy current coil 14.

Further, change in resonance frequency is represented by:

$$\partial \omega_0 = -\frac{1}{2}\frac{\partial L}{L}\omega_0 \qquad (3)$$

where:
- $\partial \omega_0$ is the change in the resonance frequency of the eddy current coil 14; and
- $\partial L$ is the change in inductance of the eddy current coil 14.

Further, the quality factor (Q) of the eddy current coil 14 is represented by:

$$Q = \frac{\omega L}{R} \qquad (4)$$

and the change in the quality factor Q is represented by:

$$\partial Q = Q\frac{\partial L}{L} - Q\frac{\partial R}{R} \qquad (5)$$

where:

$$\frac{\partial L}{L}$$

is the change in the reactive component of the impedance of the eddy current coil 14; and $$\frac{\partial R}{R}$$

is the change in the resistive component R of the impedance of the eddy current coil 14.

Further the change in the reactive and resistive components may be represented by the following equations:

$$\frac{\partial L}{L} = -\gamma\frac{\partial \sigma}{\sigma} \qquad (6)$$

$$\frac{\partial R}{R} = \beta\frac{\partial \sigma}{\sigma} \qquad (7)$$

where:

$$\frac{\partial \sigma}{\sigma}$$

is the change in the conductivity of the test part 12; and
γ, β, are parametric constants.

Therefore, a change in the quality factor Q of the eddy current coil 14 may be represented by the following equation:

$$\frac{\partial Q}{Q} = -(\gamma + \beta)\frac{\partial \sigma}{\sigma} \qquad (8)$$

Further, a resonance frequency shift of the eddy current coil 14 may be represented by the following equation:

$$\frac{\partial \omega_0}{\omega_0} = \frac{\gamma}{2} \frac{\partial \sigma}{\sigma} \qquad (9)$$

Thus, the conductivity of the test part 12 may be determined using the measured Q factor and resonance shifts in accordance with the Equations 8 and 9 described above. In certain embodiments, the quality factor of the eddy current coil 14 is estimated based upon a measured signal decay of a signal from the eddy current coil 14.

In certain embodiments, calibrated specimens having conductivity slightly higher and lower than the test part 12 are used to determine quality factor vs. conductivity transduction factor of the eddy current coil 14. Thus, by obtaining such measurements at a plurality of frequencies, an accurate estimation of the depth profile of electrical conductivity of the test part is obtained.

In certain embodiments, the changes in the quality factor are larger as compared to the resonance frequency changes for a given conductivity change provided the coil size is adjusted to operate in a pre-determined operating range represented by reference numeral 126. In particular, the size of the eddy current coil in the operating range 126 such that a resistive component of an impedance of the coil increases with the electrical conductivity of the test part 12.

Figure 8:
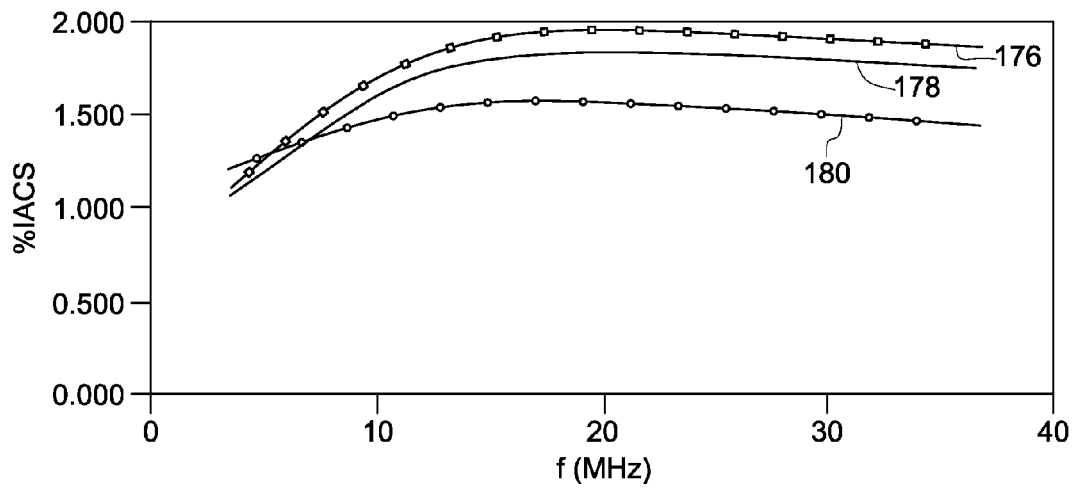
FIGS. 8-10 are graphical representations of exemplary results for conductivity profiles of test parts with different degrees of aging, obtained using the quality factor of the eddy current coil employed in the electromagnetic resonance frequency inspection system of FIG. 1.

FIG. 8 is a diagrammatical representation of an exemplary configuration 130 of the electromagnetic resonance frequency inspection system 10 of FIG. 1. In this embodiment, the eddy current system 130 includes self-contained electronics for field implementation of the resonance frequency and quality factor method for conductivity estimation as described above. The electromagnetic resonance frequency inspection system 130 includes a voltage controlled oscillator (VCO) 132 for controlling the resonance frequency of a Q-probe 134. In particular, the electromagnetic resonance frequency inspection system 130 utilizes a voltage controlled oscillator based frequency locked loop (FLL) as represented by reference numeral 136. In particular, the FLL includes a feedback circuit that generates an error signal when the VCO 132 frequency is different from the resonance frequency of the Q-probe 134. Further, this error signal is fed back into the VCO input to adjust the VCO output frequency to the resonance frequency of the test part (zero error signal when VCO frequency matches resonance frequency of the test part). Thus, this circuit locks the Q-probe 134 at its resonance frequency. The electromagnetic resonance frequency inspection system 130 includes electronics to track resonance frequency and to monitor changes in the resonance frequency $\Delta f$. Further, a second-harmonic phase locked detector estimates the quality factor Q of the Q-probe 134 at its resonance frequency.

Figure 9:
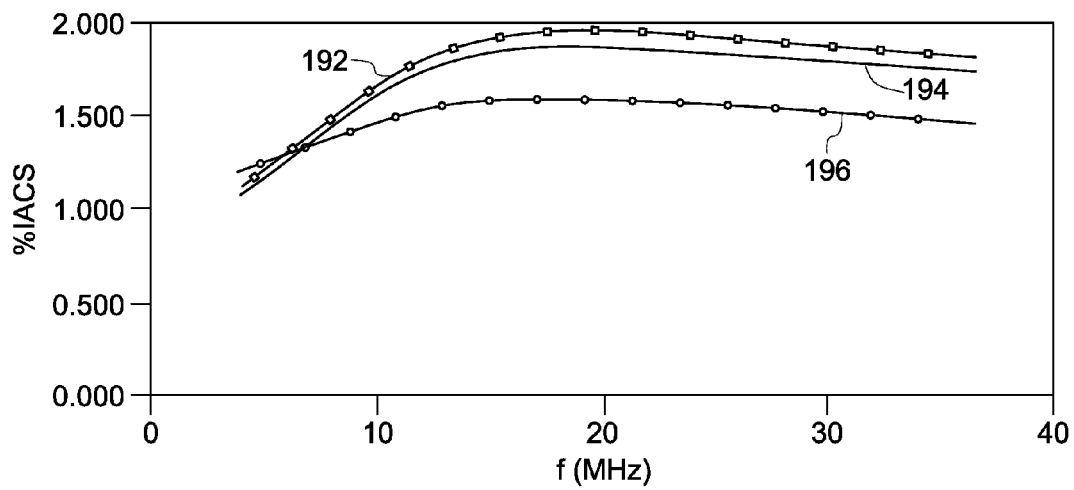
Figure 10:
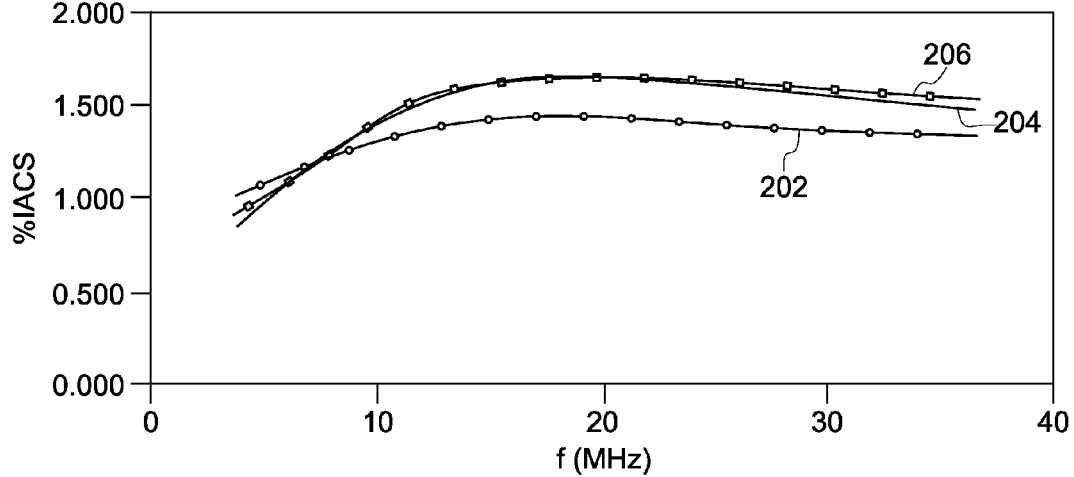

FIGS. 8-10 show sample conductivity profiles obtained for Inconel 718 alloy (IN718) test parts with varying degrees of aging. FIG. 8 depicts conductivity profiles of an IN718 test part 12 obtained using the quality factor of the coil 14 employed in the electromagnetic resonance frequency inspection system 10 of FIG. 1. The abscissa axis represents a frequency measured in mega hertz (MHz), and the ordinate axis represents the conductivity for the IN718 test part. In this example, profiles such as represented by reference numerals 176, 178, and 180 represent conductivity profiles for IN718 samples aged at about 1000° F. for about 250 hours at different shotpeening intensities. FIG. 9 is a graphical representation of exemplary results for conductivity profiles 192, 194 and 196 for IN718 samples aged at about 1000° F. for about 500 hours at different shotpeening intensities obtained using the quality factor of the eddy current probe 14. Further, FIG. 10 is a graphical representation of exemplary results for conductivity profiles 202, 204 and 206 for IN718 samples aged at about 1200° F. for about 500 hours at different shotpeening intensities obtained using the quality factor of the coil 14 employed in the electromagnetic resonance frequency inspection system 10 of FIG. As can be seen, the electrical conductivity of the aged samples initially increases with the frequency at lower frequencies but is substantially constant beyond a frequency of about 15 MHz due to relaxation of surface residual stress due to annealing effects of heat treatment.

The various aspects of the methods and systems described herein above have utility in different applications, such as in the aerospace industry. The methods and systems described above allow estimation of material properties of parts. In particular, the methods and systems utilize an estimation technique that provides accurate estimation of material properties such as electrical conductivity of a shotpeened part. These then are related to the residual stress to obtain residual stress depth profile of the shotpeened part.

Accordingly, parts that need to be re-shotpeened or replaced can be detected more reliably. In some cases, these results would indicate that the residual stress is better than expected and parts can be left in service longer or in some circumstances these methods would indicate an early relaxation of stress and the parts can be replaced before any damage or failure might occur. This can then result in timely replacement of critical engine component and parts and in some cases even prolong life of parts. Moreover, since these methods and systems employ nondestructive inspection techniques, the costs for conducting the inspection are also reduced thereby allowing all parts to be tested instead of testing just a few representative parts by traditional destructive methods that cannot be reused.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of inspecting a test part, the method comprising:
    positioning a coil on a surface of the test part;
    exciting the coil at a resonance frequency;
    determining at least one of a resonance frequency shift and a quality factor of the coil;
    estimating an electrical conductivity of the test part based on at least one of the resonance frequency shift and the quality factor of the coil; and
    adjusting a size of the coil within a pre-determined operating range such that a resistive component of an impedance of the coil increases with the electrical conductivity.

2. The method of claim 1, wherein determining the quality factor of the coil comprises estimating the quality factor based upon a measured impedance change of the coil.

3. The method of claim 1, wherein determining the quality factor of the coil comprises estimating the quality factor based upon a measured signal decay of a signal from the coil.

4. The method of claim 1, further comprising calibrating the coil using measurements of the test part and of a reference part having a known electrical conductivity.

5. A method of inspecting a test part, the method comprising:
    positioning a coil on a surface of the test part;

exciting the coil at a resonance frequency;
determining at least one of a resonance frequency shift and a quality factor of the coil;
estimating an electrical conductivity of the test part based on at least one of the resonance frequency shift and the quality factor of the coil;
adjusting the resonance frequency of the coil a plurality of times;
exciting the coil at a plurality of respective resonance frequencies for the coil;
determining at least one of the resonance frequency shift and the quality factor of the coil for each of the resonance frequencies;
obtaining a conductivity depth profile based upon at least one of the resonance frequency shifts and the quality factors of the coil at the respective resonance frequencies; and
generating a residual stress profile for the test part from the conductivity depth profile.

6. The method of claim 5, wherein adjusting the resonance frequency of the coil comprises using a plurality of eddy current coils with different resonance frequencies.

7. The method of claim 5, wherein adjusting the resonance frequency of the coil comprises
selectively coupling one or more of a plurality of capacitors to the coil.

8. The method of claim 5, wherein adjusting the resonance frequency of the coil comprises:
coupling a variable capacitor to the coil; and
changing a capacitance of the variable capacitor.

9. The method of claim 5, wherein generating the residual stress profile for the test part comprises relating the conductivity depth profile for the test part to a plurality of residual stress profile data.

10. An electromagnetic resonance frequency system for inspecting a test part, the system comprising:
a coil configured to scan the test part at a resonance frequency; and
a processor configured to estimate an electrical conductivity based upon at least one of a measured resonance frequency shift and a quality factor of the coil,
wherein the processor is further configured to:
determine a conductivity depth profile of the test part based upon at least one of the measured resonance frequency shift and the quality factor of the coil at the respective frequencies, and
generate a residual stress profile from the conductivity depth profile by relating the conductivity depth profile for the test part to a plurality of residual stress profile data.

11. The electromagnetic resonance frequency system of claim 10, further comprising a signal generator configured to energize the coil at a plurality of frequencies.

12. The electromagnetic resonance frequency system of claim 11, comprising a plurality of eddy current coils, and wherein the signal generator is configured to energize each of the eddy current coils at respective ones of the frequencies.

13. The electromagnetic resonance frequency system of claim 11, further comprising:
a plurality of capacitors coupled to the coil; and
a plurality of switches configured to selectively couple respective ones of the capacitors to the coil to adjust a resonance frequency of the coil.

14. The electromagnetic resonance frequency system of claim 11, further comprising a variable capacitor coupled to the coil for adjusting a resonance frequency of the coil.

15. The electromagnetic resonance frequency system of claim 10, wherein the processor is further configured to calibrate the coil using a plurality of measurements performed on the test part and on a reference part having a known electrical conductivity.

16. The electromagnetic resonance frequency system of claim 10, wherein the test part comprises a shotpeened part and the estimated conductivity is substantially independent of a surface roughness of the shotpeened part.

17. The electromagnetic resonance frequency system of claim 10, comprising self contained electronics having a frequency locked circuit to determine the resonance frequency shift and the quality factor of the coil.

18. A method of inspecting a test part, comprising:
selecting at least one coil having a size within a pre-determined operating range;
positioning the at least one coil on a surface of the test part;
exciting the at least one coil at a plurality of resonance frequencies; and
determining a quality factor of the at least one coil based upon a measured impedance of the coil to estimate an electrical conductivity of the test part, wherein the size of the at least one coil is selected such that a resistive component of the impedance of the coil increases with the electrical conductivity of the test part.

19. The method of claim 18, further comprising measuring a resonance frequency shift for estimating the electrical conductivity of the test part.

20. The method of claim 18, further comprising obtaining a conductivity depth profile based upon the quality factor of the coil at the respective resonance frequencies.

21. The method of claim 20, further comprising generating a residual stress profile for the test part from the conductivity depth profile.

* * * * *

UNITED STATES PATENT AND TRADEMARK OFFICE
CERTIFICATE OF CORRECTION

PATENT NO. : 7,911,205 B2  
APPLICATION NO. : 11/860629  
DATED : March 22, 2011  
INVENTOR(S) : Tralshawala et al.

Page 1 of 1

It is certified that error appears in the above-identified patent and that said Letters Patent is hereby corrected as shown below:

In Column 2, Line 30, delete "FIG." and insert -- FIG. 1. --, therefor.

Figure 7:
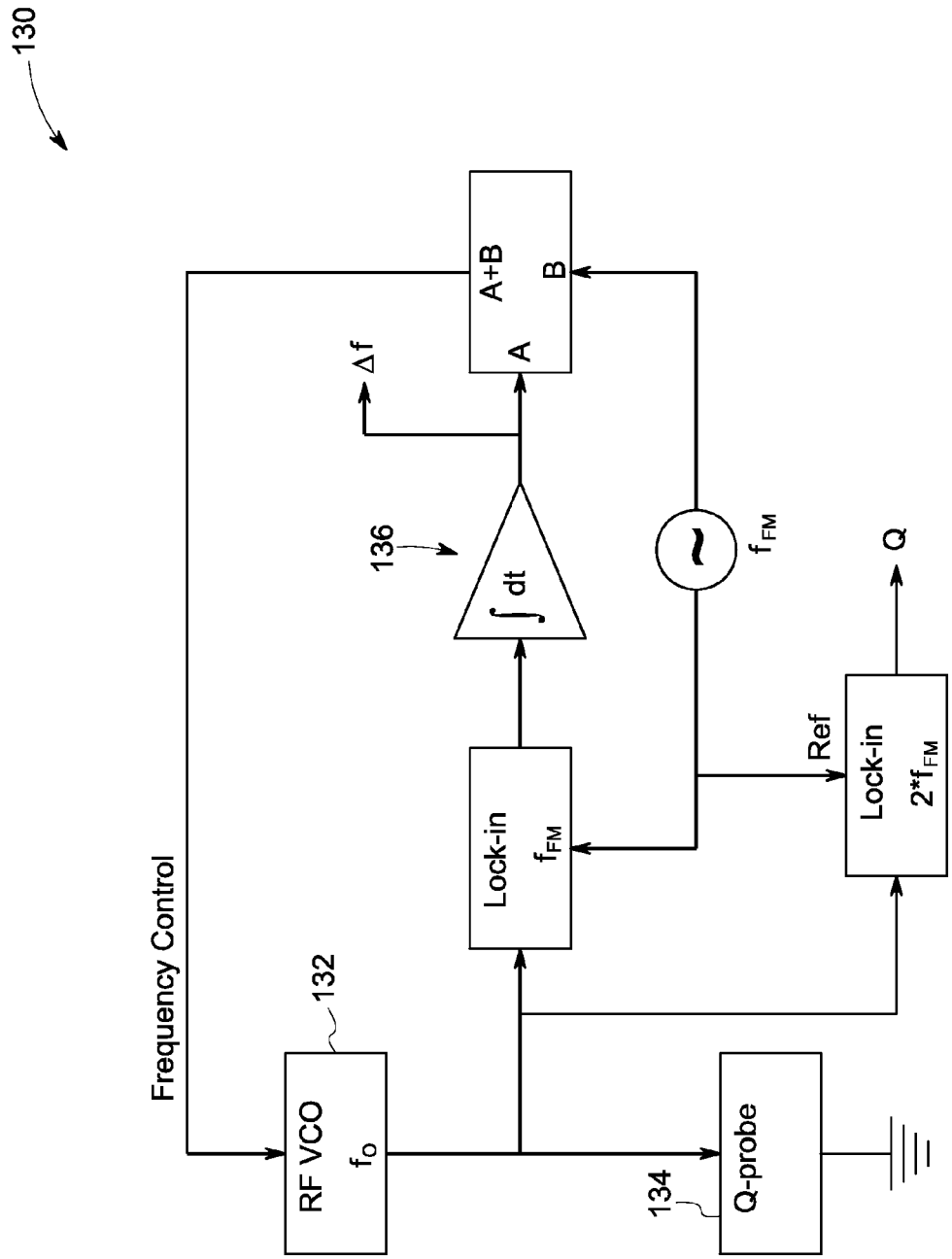
FIG. 7 is a diagrammatical representation of an exemplary configuration of the electromagnetic resonance frequency inspection system of FIG.

In Column 7, Line 27, delete "FIG. 8" and insert -- FIG. 7 --, therefor.

In Column 8, Line 7, delete "FIG." and insert -- FIG. 1. --, therefor.

In Column 10, Line 5, in Claim 12, delete "coils, and" and insert -- coils, --, therefor.

Signed and Sealed this
Sixteenth Day of August, 2011

David J. Kappos  
*Director of the United States Patent and Trademark Office*